(12) United States Patent
Surti et al.

(10) Patent No.: US 8,114,112 B2
(45) Date of Patent: Feb. 14, 2012

(54) STYLET LOCKING MECHANISM FOR MEDICAL DELIVERY DEVICES

(75) Inventors: Vihar C. Surti, Winston-Salem, NC (US); Ashwin Rajan Sakhare, Burlington, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 518 days.

(21) Appl. No.: 12/346,236

(22) Filed: Dec. 30, 2008

(65) Prior Publication Data

US 2010/0168792 A1 Jul. 1, 2010

(51) Int. Cl.
*A61B 17/34* (2006.01)
*A61M 5/178* (2006.01)

(52) U.S. Cl. .................... 606/185; 604/164.01

(58) Field of Classification Search .................. 606/184, 606/185; 604/57, 59, 68, 164.01, 164.12, 604/165.01, 165.02, 218, 223, 227–229, 604/233

See application file for complete search history.

(56) References Cited

U.S. PATENT DOCUMENTS

| | | | | |
|---|---|---|---|---|
| 2,892,457 A | * | 6/1959 | Sturtz | 604/223 |
| 3,835,835 A | * | 9/1974 | Thompson et al. | 604/218 |
| 4,263,911 A | * | 4/1981 | McCormack et al. | 604/227 |
| 4,304,231 A | | 12/1981 | Bodicky et al. | |
| 4,630,608 A | | 12/1986 | Arroyo | |
| 5,507,730 A | * | 4/1996 | Haber et al. | 604/223 |
| 5,830,229 A | | 11/1998 | Konya et al. | |
| 5,961,494 A | * | 10/1999 | Hogan | 604/223 |
| 7,235,093 B2 | | 6/2007 | Gregorich | |
| 2005/0182417 A1 | | 8/2005 | Pagano | |
| 2009/0082786 A1 | | 3/2009 | Surti | |

FOREIGN PATENT DOCUMENTS

| | | |
|---|---|---|
| EP | 0 629 381 A2 | 12/1994 |
| EP | 0 887 082 A2 | 12/1998 |
| GB | 245568 | 1/1926 |

OTHER PUBLICATIONS

Product Manual for "TriClip™ Endoscopic Clipping Device", Wilson-Cook Medical GI Endoscopy, 2005.
Product Manual for "Esophageal Z-Stent®", Wilson-Cook Medical GI Endoscopy, 2005.
Product Manual for "Evolution™ Esophageal Stent System", Wilson-Cook Medical GI Endoscopy, 2008.
International Search Report dated Apr. 28, 2010 issued in related International Patent Application No. PCT/US2009/069378.

* cited by examiner

*Primary Examiner* — Julian Woo
(74) *Attorney, Agent, or Firm* — Brinks Hofer Gilson & Lione

(57) ABSTRACT

A stylet locking mechanism for preventing axial movement of a stylet relative to a needle of a medical delivery device is disclosed. The locking mechanism comprises first and second ends that may be removably attached to the device, and a hinge for allowing the locking mechanism to be disengaged from a locking position without being completely disconnected from the delivery device.

16 Claims, 6 Drawing Sheets

STYLET LOCKING MECHANISM FOR MEDICAL DELIVERY DEVICES

FIELD OF THE INVENTION

The present invention relates generally to medical delivery devices that utilize a movable stylet extending through a sheath for deploying a tissue fixation device or prosthesis.

BACKGROUND OF THE INVENTION

Perforations in the walls of internal organs and vessels may be naturally occurring, or formed intentionally or unintentionally. In order to permanently close these perforations and allow the tissue to properly heal, numerous tissue fixation devices and methods have been developed employing sutures, adhesives, clips, staples and the like. One class of such devices is commonly referred to as T-anchors, also known as tissue anchors or visceral anchors. An exemplary tissue anchor is disclosed in U.S. Pat. No. 5,123,914, the entire contents of which are incorporated herein by reference. Such tissue anchors have been very successful in medical procedures requiring visceral wall mobilization or wall apposition.

Tissue anchors typically include a crossbar or some anchoring member connected to a suture. The anchoring member and suture may take many forms, but generally a needle is used to pierce tissue and deliver the anchoring member on one side of the tissue, leaving the suture extending back to the other side of the tissue. The sutures of one or more tissue anchors are collected and connected together, such as through tying the sutures together. A significant level of skill and coordination is required by the medical professional to deploy and subsequently tie the sutures together, especially when the tissue site is difficult to access within the body, such as in endoscopic or laparoscopic procedures.

Medical delivery devices used to deliver the tissue anchors generally comprise a sheath and a needle. The sheath has a sheath lumen sized to slidably receive the needle. The needle has a needle lumen sized to slidably receive the tissue anchor. In addition, a stylet is slidably disposed within the needle lumen to assist in the deployment of the tissue anchors. The medical delivery device may also comprise a handle that is connected to the proximal ends of the needle, sheath, and stylet for relative axial movement of these components by the medical professional. During deployment, the distal end of the stylet engages and pushes the tissue anchor out of the distal end of the needle.

The medical delivery devices are generally operable between a delivery configuration and a deployed configuration. In the delivery configuration, the needle is substantially contained within the sheath lumen, and the stylet is positioned within the needle lumen such that the proximal end of the stylet projects beyond a proximal end of the sheath. The distal end of the stylet is spaced proximally of the distal end of the needle and the tissue anchor. In this configuration, the tissue anchor remains contained within the needle. A cap is typically connected to a proximal end of the stylet.

To move the delivery device to the deployed configuration, the cap is pressed to distally advance the stylet through the needle lumen. This causes the distal end of the stylet to engage the tissue anchor and move it distally until the anchor exits the needle lumen.

A problem concerning these medical delivery devices is premature deployment of the tissue anchor. When a doctor or nurse is holding the device, there is a risk that the cap will be inadvertently or mistakenly pressed, causing the anchors to be prematurely deployed. The prior art discloses various locking mechanisms that are used to prevent the stylet from advancing through the needle lumen. However, these locking mechanisms must typically be completely disconnected and removed from the medical delivery device prior to deployment. Consequently, the locking mechanisms are often misplaced or become contaminated. These locking mechanisms may also become broken during removal. If the medical delivery device is to be re-used in the same or a subsequent procedure, then the misplaced, contaminated, or broken locking mechanism cannot be utilized. Therefore, a need exists to allow the medical delivery device to operate in the deployed configuration without having to completely disconnect and/or remove the locking mechanism from the device.

BRIEF SUMMARY OF THE INVENTION

The present invention provides a locking mechanism for preventing premature deployment of a medical delivery system and in particular, a delivery system for deploying tissue anchors. In an exemplary embodiment, the delivery system comprises a stylet slidably disposed through a needle. The mechanism comprises a body having two ends for attachment to the delivery device, and a hinge. To engage the mechanism in a locking position, the first end is connected to a proximal end of the stylet, and the second end is connected to a proximal end of the handle.

To disengage the mechanism from the locking position, the first end is disconnected from the stylet. Thereafter, the first end pivots about the hinge and away from the stylet, thereby allowing the stylet to axially move along the needle lumen to deploy the anchors. The second end remains connected to the proximal end of the handle, allowing the medical device to be in the deployment configuration without needing to completely disconnect the locking mechanism from the delivery device. Alternatively, the mechanism may be disengaged from the locking position by disconnecting the second end from the handle. Thereafter, the second end pivots about the hinge and away from the handle, thereby allowing the stylet to axially move along the needle lumen to deploy the anchors. The first end remains connected to the proximal end of the stylet, allowing the medical device to be in the deployment configuration without needing to completely disconnect the locking mechanism from the delivery device.

The first and second ends connect to the medical device via a snap-fit design, which allows the ends to be connected to and disconnected from the device numerous times. Thus, the locking mechanism can be engaged to and disengaged from the locking position numerous times without ever having both ends disconnected from the medical device. Alternatively, the snap-fit connection at both ends allows the mechanism to be completely disconnected by disconnecting both ends, and subsequently reconnected in an engaged locking position by reconnecting both ends, or reconnected in the disengaged position by connecting the second end to the handle but not connecting the first end, or by connecting the first end to the stylet but not connecting the second end to the handle.

In one embodiment of the locking mechanism, the hinge is a mechanical hinge. In such an embodiment, the body comprises two separate portions that interconnect to form the hinge, allowing one portion to move relative to the other. In a second embodiment of the locking mechanism, the hinge is a living hinge. In such an embodiment, the body comprises only one piece having a flexible portion that enables one end to move relative to the other.

The present invention is described as a locking mechanism for tissue anchor delivery devices, where movement of the stylet in relation to the needle is prevented. However, the invention may be adapted to serve as a locking mechanism for any medical delivery device used for permanent or temporary deployment of a medical object to a target area of the human body. Such an adaptation may include engagement with any medical device having two or more portions where one moves relative to another, such as the stylet relative to the sheath, the stylet relative to the handle, the needle relative to the sheath, the needle relative to the handle, the sheath relative to the handle, the handle having two portions where one moves relative to the other, or any combination thereof. An example of such a medical delivery device is Wilson-Cook Medical, Inc.'s TriClip® endoscopic clipping device.

DETAILED DESCRIPTION OF THE INVENTION

Figure 1A:
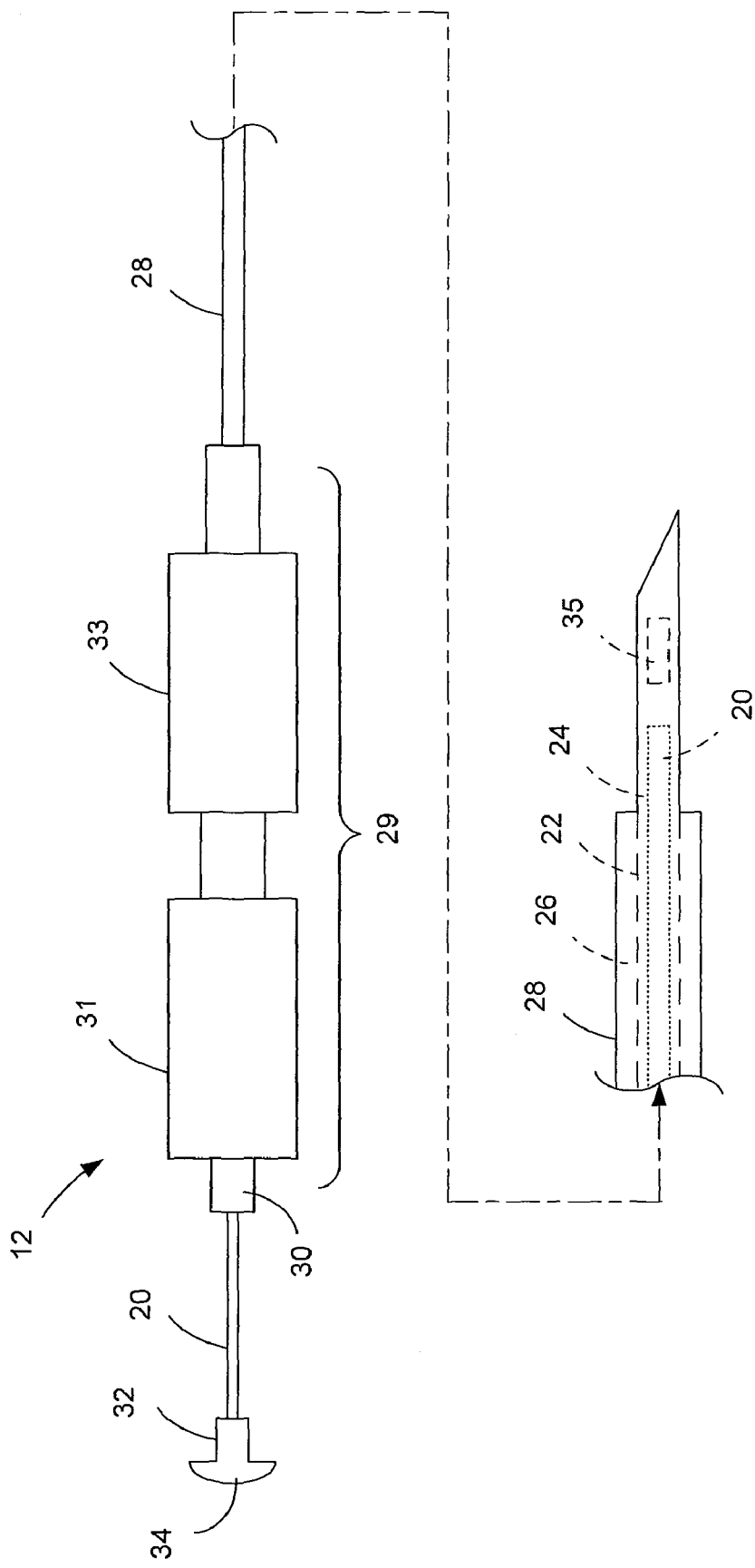
FIG. 1A is a side view of the medical delivery device positioned in the delivery configuration.
Figure 1B:
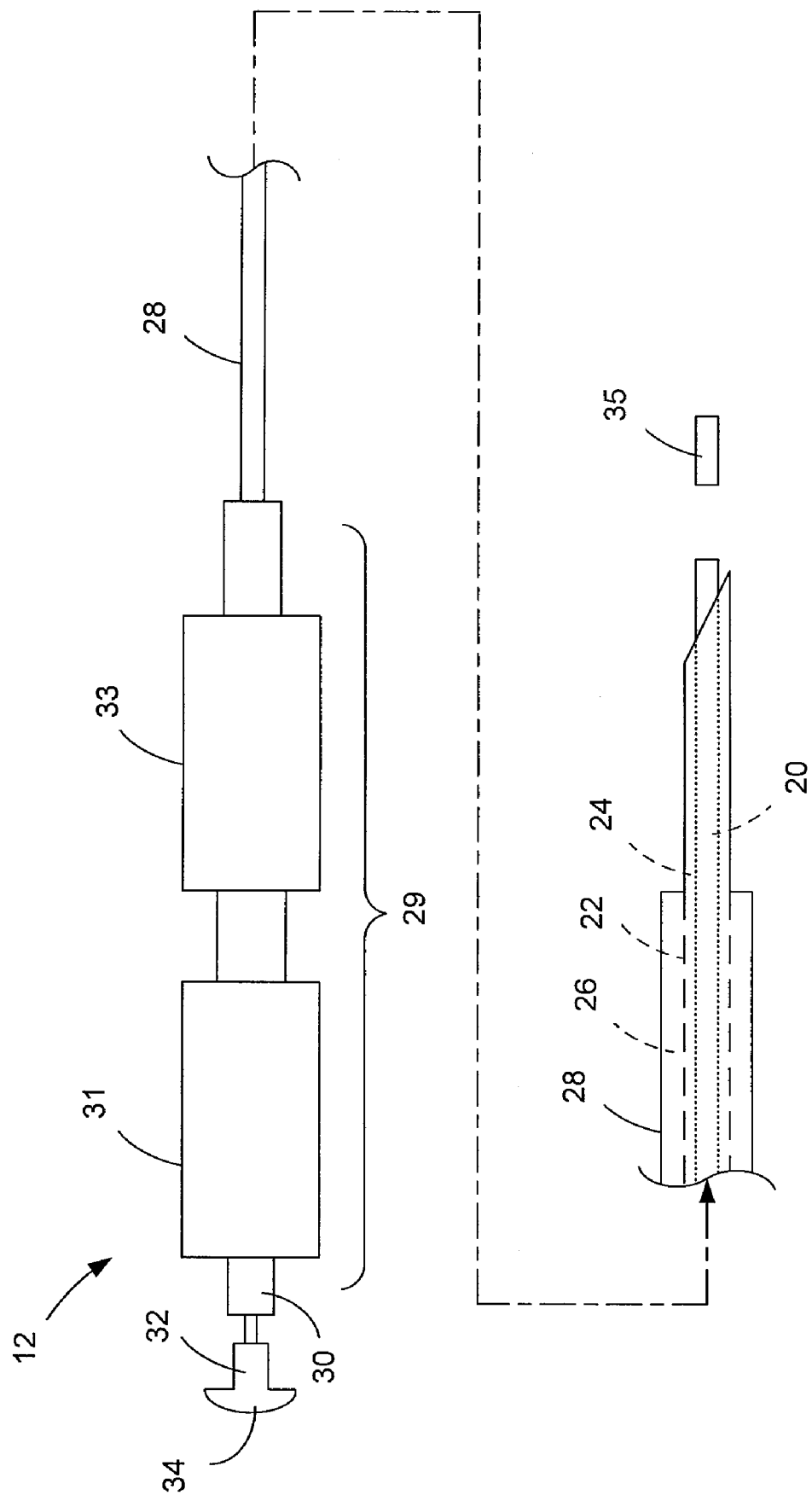
FIG. 1B is a side view similar to 1B and in partial cross-section, but showing a deployed configuration of the medical delivery device.

Turning now to the figures, FIG. 1A and FIG. 1B depict a tissue anchor delivery device 12 for which the present invention is utilized. The delivery device 12 generally comprises a stylet 20, which is slidably disposed within a needle lumen 24 of a needle 22, and in which the needle 22 is slidably disposed within a sheath lumen 26 of a sheath 28. The medical delivery device 12 may also comprise a handle 29 that is connected to the proximal ends of the needle 22, sheath 28, and stylet 20 for relative axial movement of these components by the medical professional. The handle 29 may comprise a proximal handle portion 31 fixedly connected to the needle 22, and a distal handle portion 33 fixedly connected to the sheath 28, and wherein the stylet 20 movably extends through the first and second handle portions 31, 33. The delivery device 12 is generally operable between a delivery configuration and a deployed configuration. FIG. 1A depicts the delivery device 12 in the delivery configuration. When the delivery device 12 is positioned in the delivery configuration, a portion of the stylet 20 extends proximally from a handle connecting portion 30 located at the proximal end of the handle 29. A stylet connecting portion 32 located at the proximal end of the stylet 20 may be in connection with a cap 34. To place the delivery device 12 in the deployed configuration, shown in FIG. 1B, the cap 34 is pressed in a distal direction, causing the stylet 20 to move axially along the needle lumen 24 and deploy a tissue anchor 35 situated therein.

Figure 2:
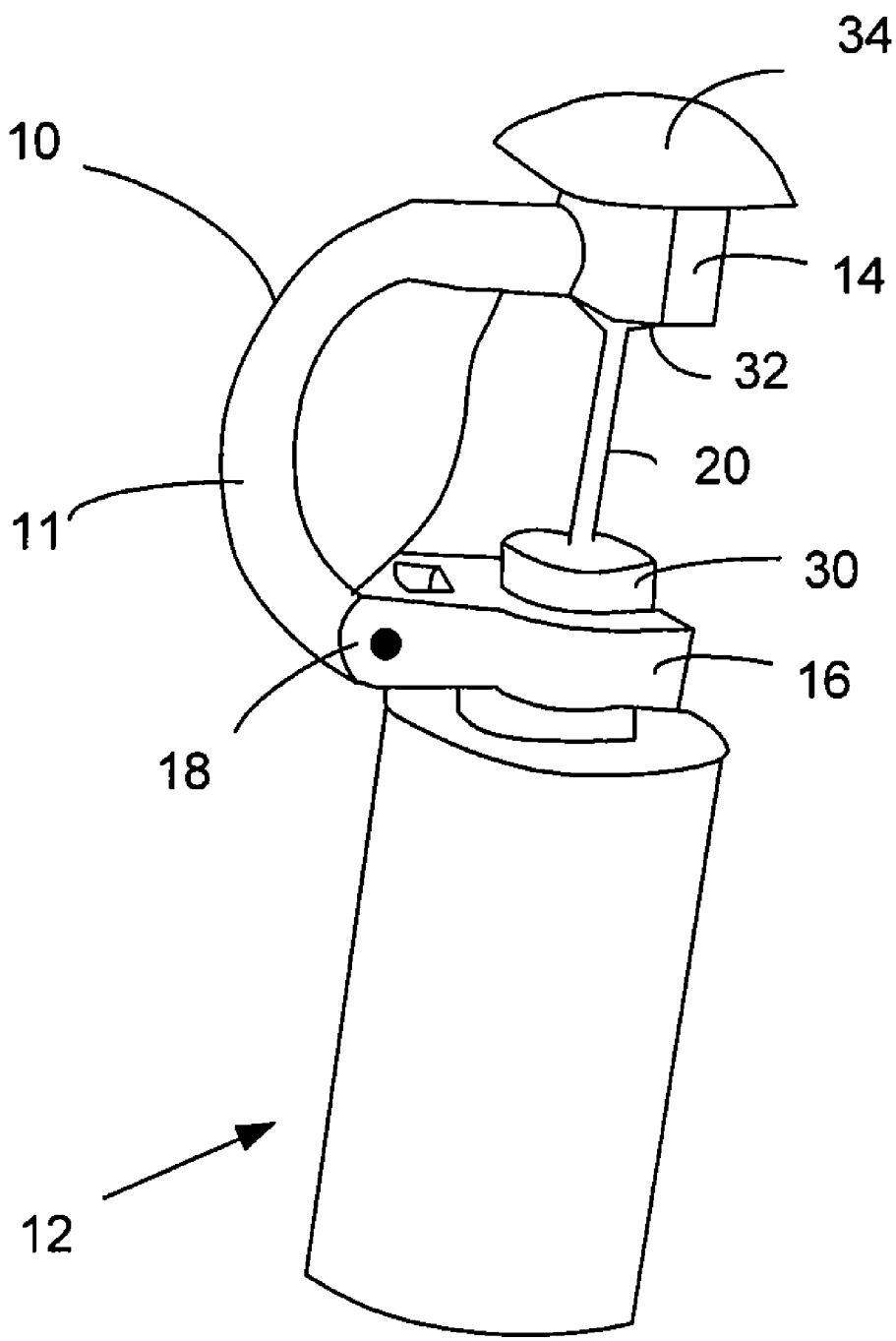
FIG. 2 is a side view of the stylet locking mechanism engaged in the locking position and completely connected to the tissue anchor delivery device positioned in the delivery configuration.

FIG. 2 depicts a stylet locking mechanism 10 completely connected to the delivery device 12. The stylet locking mechanism 10 generally comprises a body 11 having a first end 14, a second end 16, and a hinge 18. The stylet locking mechanism 10 is designed for preventing axial movement of the stylet 20 in relation to the needle 22 of the delivery device 12 when in complete connection with the delivery device 12.

When the delivery device 12 is positioned in the delivery configuration, the locking mechanism 10 may be engaged in a locking position by being completely connected to the delivery device 12, as shown in FIG. 2. In particular, the locking mechanism 10 is in complete connection with the delivery device 12 when the first end 14 of the locking mechanism 10 is in connection with the stylet connecting portion 32 and the second end 16 of the locking mechanism 10 is in connection with the handle connecting portion 30. When the locking mechanism 10 is engaged in a locking position, the stylet 20 is prevented from moving axially along the needle lumen 24 to deploy the a tissue anchor 35.

Figure 3:
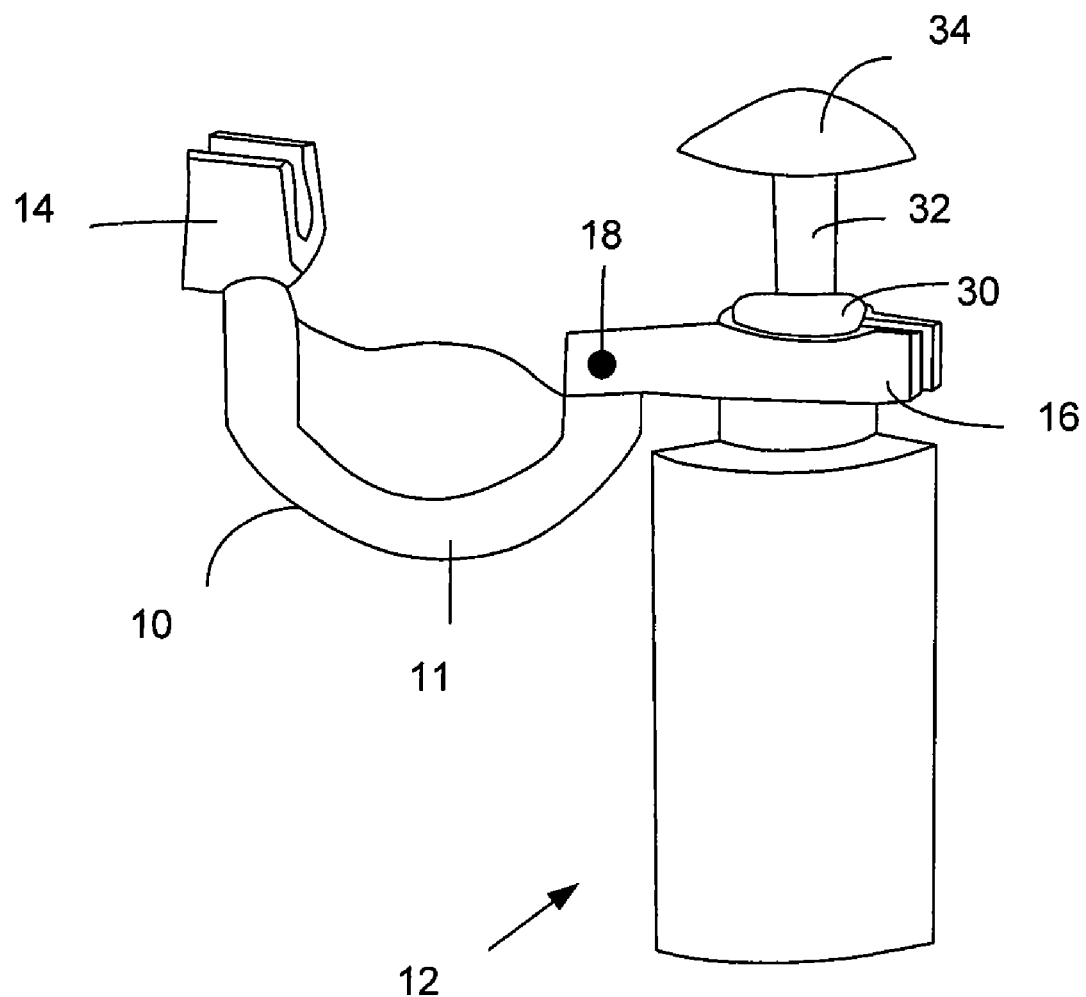
FIG. 3 is a side view of the stylet locking mechanism of FIG. 1 disengaged from the locking position, but connected to the tissue anchor delivery device, the delivery device positioned in the deployed configuration.

FIG. 3 depicts the locking mechanism 10 in partial disconnection and disengaged from the delivery device 12, and the delivery device 12 positioned in the deployed configuration. To configure the delivery device 12 in the deployed configuration, the locking mechanism 10 is disengaged from the locking position. To be disengaged, the locking mechanism 10 may be in either complete disconnection from the delivery device 12, or in partial disconnection from the delivery device 12. When the locking mechanism 10 is in complete disconnection from the delivery device 12, the first end 14 of the locking mechanism 10 is not in connection with the stylet connecting portion 32, and the second end 16 of the locking mechanism 10 is not in connection with the handle connecting portion 30. In other words, the locking mechanism 10 has been removed from the delivery device 12. When the locking mechanism 10 is in partial disconnection, the first end 14 of the locking mechanism 10 is not in connection with the stylet connecting portion 32, but the second end 16 of the locking mechanism 10 is in connection with the handle connecting portion 30. Alternatively, to be in partial disconnection from the delivery device 12, the second end 16 is not in connection with the handle connecting portion 30, but the first end 14 is in connection with the stylet connecting portion 32.

The delivery device 12 may be in the deployed configuration without complete disconnection of the locking mechanism 10 through operation of the hinge 18. When the first end 14 of the locking mechanism 10 is disconnected from the stylet connecting portion 32, but the second end 16 of the locking mechanism 10 remains in connection with handle connecting portion 30, the first end 14 may move pivotally about the hinge 18 and away from the stylet 20, thereby allowing the stylet 20 to axially move along the needle lumen 24. In an embodiment where the proximal end of the stylet 20 is in connection with the cap 34, the first end 14 will move pivotally about the hinge 18 and rest at a position such that the cap 34 does not come into contact with the locking mechanism 10 as the stylet 20 axially moves along the needle lumen 24.

Alternatively, the locking mechanism 10 may be in partial disconnection and disengaged from the delivery device 12 when the first end 14 of the locking mechanism 10 remains in connection with the stylet locking portion 32, but the second end 16 of the locking mechanism 10 is disconnected from the handle connecting portion 30. When the first end 14 is connected, but the second end 16 is not connected, the second end 16 may move pivotally about the hinge 18 and away from the handle 29, thereby allowing the stylet 20 to axially move along the needle lumen 24.

After the locking mechanism 10 has been disengaged and partially disconnected from the delivery device 12, the locking mechanism 10 may be re-engaged in the locking position, as shown in FIG. 2. To re-engage the locking mechanism 10 when the first end 14 has been disconnected from the stylet locking portion 32, but the second end 16 remains in connection with the handle connecting portion 30, the first end 14 is moved pivotally about the hinge 18 and thereafter connected to the stylet locking portion 32. To re-engage the locking mechanism 10 when the second end 16 has been disconnected from the handle connecting portion 30, the second end 16 is moved pivotally about the hinge 18 and thereafter connected to the handle connecting portion 32. It will be understood that when the delivery device 12 is deployed after disengaging the locking mechanism 10, the medical professional will return the delivery device 12 to the delivery configuration prior to re-engaging the locking mechanism 10.

Figure 4A:
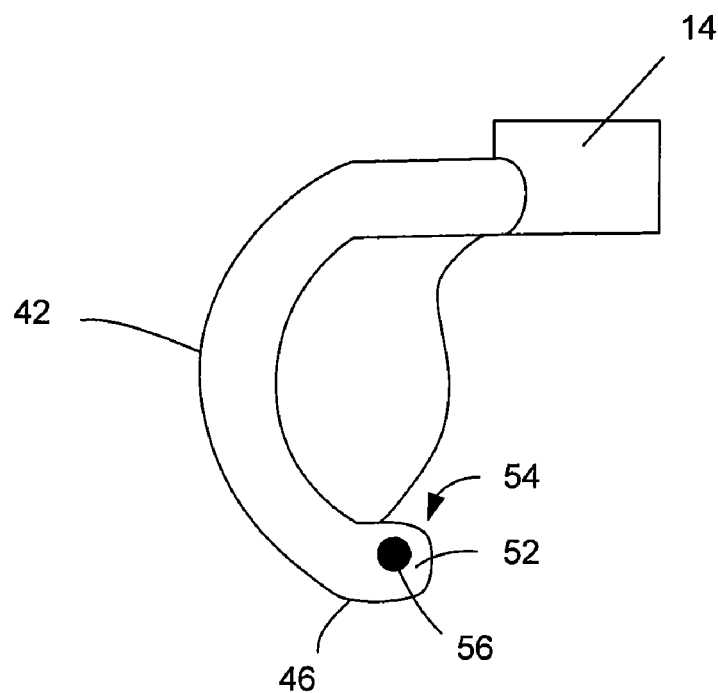
FIG. 4A is a fragmentary view of the first portion of the body of the stylet locking mechanism of FIG. 2.
Figure 4B:
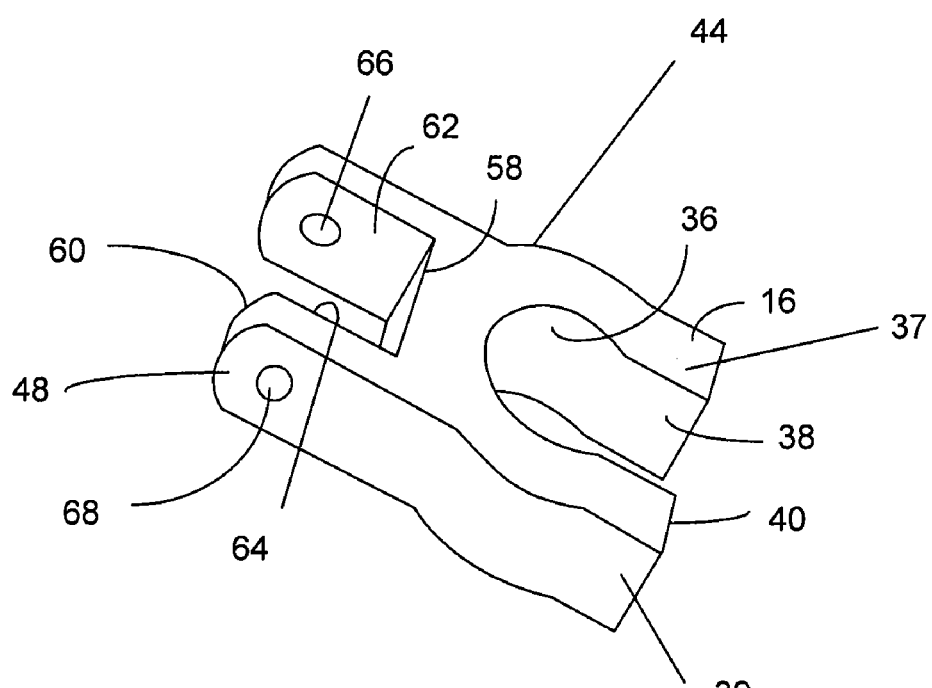
FIG. 4B is a fragmentary view of the second portion of the body of the stylet locking mechanism of FIG. 2.

In one embodiment, the ends 14, 16 of the locking mechanism 10 may be removably in connection with the delivery device 12 by means of a snap-fit design, shown in FIG. 4B. The snap-fit design allows the ends 14, 16 to be connected to, and thereafter disconnected from and reconnected to their respective connecting portions 32, 30 several times. In the snap-fit design, an inner portion 36 of the ends 14, 16 is designed to conform to the cross-sectional shape of the connecting portions 32, 30. Also, in the snap-fit design, the ends 14, 16 each have resilient arm members 37, 39, and an opening 38, the width of the opening being defined as the distance between the arm members 37, 39, as shown in FIG. 4B. The opening 38 has an original width less than the maximum widths (e.g., cross-sectional diameter) of the respective connecting portions 32, 30 and ends 14, 16.

FIG. 4B depicts one embodiment of the second end 16 having a circular-shaped inner portion 36 to conform to a circular cross-section of the handle connecting portion 30. The diameter of the circular inner portion 36 is substantially the same as the diameter of the circular cross-section of the handle connecting portion 30 for securely connecting the second end 16 to the handle connecting portion 30. The width of the opening 38 is less than the diameter of the circular inner portion 36.

The following discussion describes how the second end 16 may be connected to the handle connecting portion 30 in accordance with a snap-fit design. One of ordinary skill in the art would understand that the first end 14 may be connected to the stylet connecting portion 32 in substantially the same way. To connect the second end 16 to the handle connecting portion 30, an outer portion 40 of the arms 37, 39 is biased against the handle connecting portion 30 at the opening 38 with at least a threshold force. Biasing the arm members 37, 39 against the handle connecting portion 30 with at least the threshold force causes the opening 38 to widen, allowing the sheath connecting portion 30 to frictionally slide past the outer portion 40 and through the opening 38 until the handle connecting portion 30 is securely within the inner portion 36. When the handle connecting portion 30 is completely within the inner portion 36, the resilient arms 37, 39 are no longer biased and move back to their original position, allowing for a secure connection.

The second end 16 may be disconnected to the handle connecting portion 30 in a similar manner. To disconnect the second end 16 from the handle connecting portion 30, the inner portion 36 is biased against the handle connecting portion 30 at the opening 38. When at least the threshold force is applied, the opening 38 widens, causing the handle connecting portion 30 to frictionally slide past the inner portion 36 and through the opening 38 until the handle connecting portion 30 and the second end 16 are separated.

The snap-fit design allows the ends 14, 16 to be connected to, disconnected from, and reconnected to their respective connecting portions 32, 30 numerous times. Accordingly, the locking mechanism 10 may transition between engaged and completely connected, disengaged and completely disconnected, and disengaged and partially disconnected positions numerous times and in no particular order.

FIGS. 4A and 4B depict one embodiment, wherein the body 11 comprises two separate portions, a first body portion 42 and a second body portion 44, that may be interconnected to form the hinge 18, and wherein the hinge 18 is a mechanical hinge. As shown in FIG. 4A, the first body portion 42 comprises the first end 14, and further comprises a first hinge end 46, which is located opposite the first end 14. As shown in FIG. 4B, the second body portion 44 comprises the second end 16, and further comprises a second hinge end 48, which is located opposite the second end 16. The first hinge end 46 and the second hinge end 48 may be interconnected to form the hinge 18. The first hinge end 46 and the second hinge end 48 may be configured in any manner to form the mechanical hinge, such that when interconnected, the first body portion 42 and the second body portion 44 may pivotally move about the hinge 18 relatively to each other. As shown in FIG. 4A, in the preferred embodiment, the first hinge end 46 comprises a first hinge end body 52, a left knob 54, and a right knob 56, where the left knob 54 and the right knob 56 protrude from opposite lateral ends of the first hinge end body 52. As shown in FIG. 4B, the second hinge end 48 comprises a second hinge end slot 58 having a second hinge end opening 60, a second hinge end left wall 62, and a second hinge end right wall 64. The second hinge end left wall 62 comprises a left socket 66 for receiving the left knob 54, and the second hinge end right wall 64 comprises a right socket 68 for receiving the right knob 56. To interconnect the first hinge end 46 and the second hinge end 48, the first hinge end body 52 is inserted into the second hinge end slot 58, and positioned at a location where the left knob 54 is engaged to the left socket 66, and the right knob 56 is engaged to the right socket 68.

Figure 5:
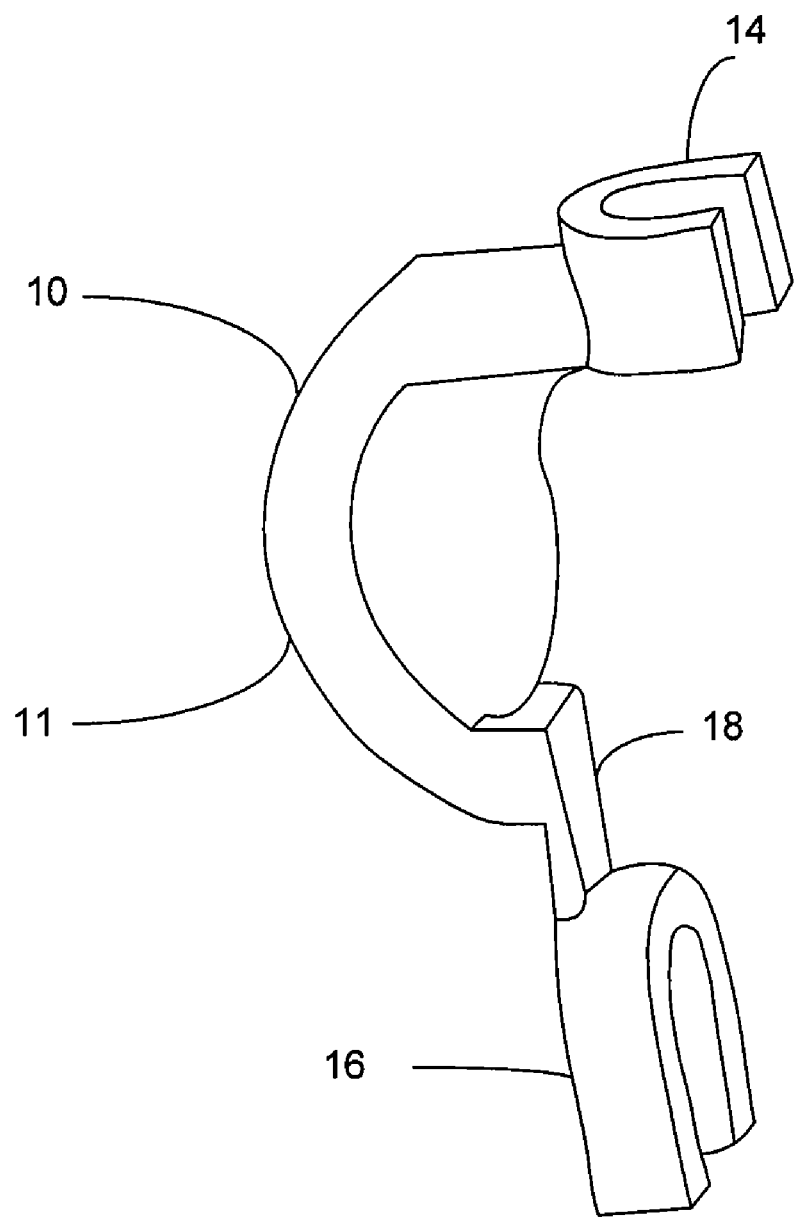
FIG. 5 is a side view of an alternative embodiment of the stylet locking mechanism.

FIG. 5 depicts an alternative embodiment, wherein the locking mechanism 10 has a unitary construction, and the hinge 18 is a living hinge. The hinge 18 is defined as being a relatively thin portion of the locking mechanism 10 that allows the locking mechanism 10 to be in compete connection with the delivery device 12 and engaged in the locking position, and alternatively, in partial disconnection and disengaged from the delivery device.

Although the locking mechanism of the present invention has been described in use with a tissue anchor delivery device, it should be understood that the locking mechanism can be used with other types of medical delivery systems comprising an inner member axially slidable within an outer member. For example, the locking mechanism may be utilized by a delivery device for deploying a self-expanding stent, where the self-expanding stent is disposed within a sheath lumen and about an inner catheter.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A locking mechanism for a medical delivery device comprising an elongate inner member movably disposed within an elongate outer member, and a deployable device disposed within the outer member near a distal end of the inner member, wherein movement of the inner member in a distal direction relative to the outer member deploys the deployable device from a distal end of the outer member, the locking mechanism comprising:
    a body having a first end adapted to be removably connected to an end cap of the inner member, a second end adapted to be removably connected to a hub of the outer member, and a hinge for permitting movement of the first end relative to the second end,
    wherein axial movement of the inner member relative to the outer member is prevented when the first end is connected to the inner member and the second end is connected to the outer member,
    wherein axial movement of the inner member relative to the outer member is permitted when one of the first end and the second end is disconnected from the delivery device, and the other of the first end and the second end is connected to the delivery device,
    wherein the locking mechanism is detached from the delivery device when the first end and the second end are each disconnected from the delivery device, and
    wherein the first and second ends each have a snap-fit design.

2. The locking mechanism of claim 1, wherein the body comprises a first portion and a second portion, the first portion comprises the first end, the second portion comprises the second end, and the hinge is formed by an interconnection between the first and second portions.

3. The locking mechanism of claim 2, wherein the first portion further comprises a first hinge end located opposite the first end, the second portion further comprises a second hinge end located opposite the second end, and the first and second portions are interconnected at the first and second hinge ends.

4. The locking mechanism of claim 2, wherein the hinge comprises a mechanical hinge.

5. The locking mechanism of claim 4, wherein the mechanical hinge comprises a plurality of knobs engaged with a plurality of sockets, the plurality of knobs protruding from opposite sides of one of the first portion and the second portion, and the plurality of sockets located at opposite sides of the other of the first portion and the second portion.

6. The locking mechanism of claim 1, wherein the locking mechanism comprises a unitary construction and the hinge comprises a living hinge.

7. The locking mechanism of claim 1, wherein the outer member comprises a needle and the inner member comprises a stylet, and further wherein the delivery device comprises a sheath disposed about the needle, the needle being slidably disposed within a sheath lumen of the sheath.

8. The locking mechanism of claim 7, wherein the medical delivery device further comprises a handle operably connected to each of the sheath and the needle, the handle being configured for axial movement of the sheath relative to the needle.

9. The locking mechanism of claim 8, wherein the handle comprises a proximal handle portion fixedly connected to the needle, and a distal handle portion fixedly connected to the sheath, the proximal handle portion being axially movable relative to the distal handle portion, and further wherein the stylet movably extends through the proximal and distal handle portions.

10. The locking mechanism of claim 9, wherein the first end of the locking mechanism is configured to be removably connected to a proximal end of the stylet, the proximal end of the stylet being disposed proximally of the proximal handle portion, and the second end is configured to be removably connected to a proximal end of the proximal handle portion.

11. The locking mechanism of claim 7, wherein the medical delivery device is a tissue anchor delivery device and the deployable device is a tissue anchor.

12. A locking mechanism for a tissue anchor delivery device comprising an elongate stylet movably disposed within an elongate needle, the needle being movably disposed within an elongate sheath, a handle operably connected to the needle and the sheath and configured to provide axial movement therebetween, and a tissue anchor disposed within the needle near a distal end of the stylet, wherein movement of the stylet in a distal direction relative to the needle deploys the tissue anchor from a distal end of the needle, the locking mechanism comprising:
    a first portion comprising a first end adapted to be removably connected to an end cap fixedly connected to a proximal end of the stylet;
    a second portion comprising a second end adapted to be removably connected to a hub of the handle, the hub being operably connected to the needle; and
    a hinge connecting the first portion and the second portion, the hinge permitting the first portion to pivot relative to the second portion,
    wherein the locking mechanism is configured to be fully engaged with the delivery device, partially engaged with the delivery device, and fully disengaged from the delivery device,
    wherein the locking mechanism is fully engaged with the delivery device when the first end and the second end are each connected to the delivery device,
    wherein the locking mechanism is partially engaged with the delivery device when one of the first end and the second end is disconnected from the delivery device, and the other of the first end and the second end is connected to the delivery device;
    wherein the locking mechanism is fully disengaged from the delivery device when the first and second ends are each disconnected from the delivery device;
    wherein axial movement of the stylet relative to the needle is permitted when the locking mechanism is either partially engaged with or fully disengaged from the delivery device;
    wherein axial movement of the stylet relative to the needle is prevented when the locking mechanism is fully engaged with the delivery device;
    wherein the hinge permits the locking mechanism to move between the fully engaged and partially engaged configurations, and
    wherein the first and second ends each have a snap-fit design configured to removably engage a portion of the delivery device.

13. The locking mechanism of claim 12, wherein the snap-fit design comprises a pair of opposing arms that are configured to engage the delivery device and prevent axial movement therebetween, the arms being sufficiently flexible to allow attachment to and removable from the delivery device.

14. The locking mechanism of claim 12, wherein the hinge comprises a mechanical hinge.

15. The locking mechanism of claim 12, wherein the hinge comprises a living hinge.

16. The locking mechanism of claim 12, wherein the handle comprises a proximal handle portion fixedly connected to the needle, and a distal handle portion fixedly connected to the sheath, and further wherein the stylet movably extends through the proximal and distal handle portions, the proximal end of the stylet being disposed proximally of the proximal and distal handle portions.

* * * * *